United States Patent
Liu (10) Patent No.: US 12,420,041 B2
(45) Date of Patent: Sep. 23, 2025

(54) METHOD AND DEVICE FOR BREATHING RECOGNITION, VENTILATION APPARATUS, AND STORAGE MEDIUM

(71) Applicant: SHENZHEN MINDRAY BIO-MEDICAL ELECTRONICS CO., LTD., Shenzhen (CN)

(72) Inventor: Jinglei Liu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 1175 days.

(21) Appl. No.: 17/315,236

(22) Filed: May 7, 2021

(65) Prior Publication Data

US 2021/0260318 A1    Aug. 26, 2021

Related U.S. Application Data

(63) Continuation of application No. PCT/CN2018/114635, filed on Nov. 8, 2018.

(51) Int. Cl.
*A61M 16/00*    (2006.01)

(52) U.S. Cl.
CPC ...... *A61M 16/024* (2017.08); *A61M 16/0003* (2014.02); *A61M 2016/0015* (2013.01); *A61M 2205/3334* (2013.01)

(58) Field of Classification Search
CPC .... A61M 16/00–0003; A61M 16/0051; A61M 16/0057; A61M 16/021–024; A61M 2016/0015–0042; A61M 2205/3331–3334
See application file for complete search history.

(56) References Cited

U.S. PATENT DOCUMENTS

| | | | |
|---|---|---|---|
| 2005/0087190 A1 | 4/2005 | Jafari et al. | |
| 2008/0257349 A1 | 10/2008 | Hedner et al. | |
| 2018/0133418 A1* | 5/2018 | Brand | A61M 16/0006 |
| 2018/0317808 A1* | 11/2018 | Wang | A61B 5/0816 |
| 2019/0217030 A1* | 7/2019 | Burgess | A61M 16/16 |

(Continued)

FOREIGN PATENT DOCUMENTS

| | | |
|---|---|---|
| CN | 101366672 A | 2/2009 |
| CN | 102655903 A | 9/2012 |
| CN | 103977491 A | 8/2014 |

(Continued)

OTHER PUBLICATIONS

Second Office Action issued in related Chinese Application No. 201880098692.4, mailed Jun. 28, 2024, 4 pages.

(Continued)

*Primary Examiner* — Rachel T Sippel
(74) *Attorney, Agent, or Firm* — Morgan, Lewis & Bockius LLP (57) ABSTRACT

This disclosure provides a breathing recognition method applicable in a ventilation apparatus. In the breathing recognition method, an airway pressure and a gas flow rate can be acquired during mechanical ventilation; correlation data corresponding to the airway pressure and the gas flow rate can be determined according to the airway pressure and the gas flow rate; and a breathing state of a patient can be recognized according to a change in the correlation data.

20 Claims, 5 Drawing Sheets

---

Acquire an airway pressure and a gas flow rate during mechanical ventilation — S101

Determine correlation data corresponding to the airway pressure and the gas flow rate according to the airway pressure and the gas flow rate — S102

Recognize a breathing state of a patient according to a change in the correlation data — S103

(56) References Cited

U.S. PATENT DOCUMENTS

2020/0054520 A1* 2/2020 Johnson ................ A61B 5/091
2020/0108215 A1* 4/2020 Nakai ................ A61M 16/026

FOREIGN PATENT DOCUMENTS

| CN | 106029141 A | 10/2016 |
| CN | 106139349 A | 11/2016 |
| CN | 107029326 A | 8/2017 |
| CN | 108619597 A | 10/2018 |

OTHER PUBLICATIONS

First Office Action issued in related Chinese Application No. 201880098692.4, mailed Nov. 28, 2023, 7 pages.
Extended European Search Report issued in related European Application No. 18939186.5, mailed Oct. 19, 2021, 11 pages.
Hite Robert Duncan: "2.4 Modes of mechanical ventilation" in "A Practical Guide to Mechanical Ventilation", Dec. 31, 2011, John Wiley & Sons, Incorporated, XP055849573, pp. 141-162.
Chatburn Robert L et al: "Special Articles Classification of Ventilator Modes: Update and Proposal for Implementation", Care Daedalus Enterprises, vol. 52, No. 3, Mar. 31, 2007, XP055849574, pp. 301-323.
Anonymous: "Ventilator—Wikipedia", Oct. 8, 2018, XP055849575, Retrieved from the Internet: URL: https://en.wikipedia. org/w/index. php? title=Ventilator & oldid = 862900865, retrieved on Oct. 8, 2021.
International Search Report issued in corresponding International Application No. PCT/CN2018/114635, mailed Aug. 20, 2019, 4 pages.
Communication issued in related European Application No. 18939186. 5, mailed Oct. 30, 2024, 5 pages.

* cited by examiner

METHOD AND DEVICE FOR BREATHING RECOGNITION, VENTILATION APPARATUS, AND STORAGE MEDIUM

CROSS REFERENCE TO RELEGATED APPLICATIONS

This application is a by-pass continuation of Patent Cooperation Treaty Application No. PCT/CN2018/114635, filed on Nov. 8, 2018, the entire content of which is hereby incorporated by reference.

TECHNICAL FIELD

Embodiments of the disclosure relate to the technical field of medical equipment, and in particular, to a breathing recognition method and device, a ventilation apparatus, and a storage medium.

BACKGROUND

In the process of mechanically ventilating a patient by using ventilation apparatuses such as ventilators and anesthesia machines, it is necessary to recognize the patient's breathing in real time, so as to determine whether the patient is subjected to asphyxia or has other conditions, or to trigger a corresponding ventilation mode to achieve the aim of patient-ventilator synchronization.

At present, there are a plurality of breathing recognition methods: performing recognition based on a diaphragmatic electromyogram, and determining the patient's breathing by measuring the electrical activity of the diaphragm; or, performing recognition based on an abdominal sensor, and monitoring the patient's abdominal movement with the abdominal sensor to recognize whether the patient has spontaneous breathing.

However, the breathing recognition methods above are affected by the outside environment, the ventilation apparatus itself, or the testing difficulty, which may result in inaccurate breathing recognition or even misrecognition.

SUMMARY

In order to solve the above technical problems, embodiments of the disclosure provide a breathing recognition method and device, a ventilation apparatus, and a storage medium, which can recognize a breathing state of a patient according to a change in correlation data of an airway pressure and a gas flow rate when the patient is mechanically ventilated, so as to effectively reduce the influence of interference signals on breathing recognition and improve the accuracy of breathing recognition.

The technical solutions of the embodiments of the disclosure may be implemented as follows.

An embodiment of the disclosure provides a breathing recognition method applicable to a ventilation apparatus, the method including:
  acquiring an airway pressure and a gas flow rate during mechanical ventilation;
  determining correlation data corresponding to the airway pressure and the gas flow rate according to the airway pressure and the gas flow rate; and
  recognizing a breathing state of a patient according to a change in the correlation data.

In the above solution, determining correlation data corresponding to the airway pressure and the gas flow rate according to the airway pressure and the gas flow rate includes:
  performing correlation calculation on the airway pressure and the gas flow rate according to a preset signal sampling rate and a preset sampling duration, so as to obtain the correlation data.

In the above solution, performing correlation calculation on the airway pressure and the gas flow rate according to a preset signal sampling rate and a preset sampling duration so as to obtain the correlation data includes:
  acquiring a first sampled value corresponding to the airway pressure and a second sampled value corresponding to the gas flow rate respectively within the preset sampling duration according to the preset signal sampling rate; and
  performing the correlation calculation on the first sampled value and the second sampled value to obtain the correlation data.

In the above solution, the breathing state of the patient includes at least one of spontaneous inhalation and spontaneous exhalation, and after recognizing the breathing state of the patient according to the change in the correlation data, the method further includes:
  controlling the ventilation apparatus to switch a ventilation mode according to the recognized breathing state of the patient.

In the above solution, controlling the ventilation apparatus to switch a ventilation mode according to the recognized breathing state of the patient includes:
  triggering the ventilation apparatus to enter into an inhalation ventilation mode when the breathing state of the patient changes from spontaneous exhalation to spontaneous inhalation; and
  triggering the ventilation apparatus to enter into an exhalation ventilation mode when the breathing state of the patient changes from spontaneous inhalation to spontaneous exhalation.

In the above solution, the gas flow rate is a respiratory flow rate, and recognizing a breathing state of a patient according to a change in the correlation data includes:
  determining that the breathing state of the patient is spontaneous inhalation when the correlation data is greater than a first preset threshold; and
  determining that the breathing state of the patient is spontaneous exhalation when the correlation data is less than a second preset threshold.

In the above solution, the gas flow rate is a gas supply flow rate, and recognizing a breathing state of a patient according to a change in the correlation data includes:
  determining a parameter baseline corresponding to the correlation data;
  determining that the breathing state of the patient is spontaneous exhalation when the correlation data is greater than the parameter baseline and a difference between the correlation data and the parameter baseline is greater than a third preset threshold; and
  determining that the breathing state of the patient is spontaneous inhalation when the correlation data is less than the parameter baseline and a difference between the correlation data and the parameter baseline is greater than a fourth preset threshold.

In the above solution, determining a parameter baseline corresponding to the correlation data includes:
  calculating the correlation data in a first time period; and
  performing low-pass filtering on the correlation data in the first time period to obtain the parameter baseline.

In the above solution, the breathing state of the patient includes asphyxia, and recognizing a breathing state of a patient according to a change in the correlation data includes:

determining that the breathing state of the patient is asphyxia when the correlation data has a fluctuation range less than a preset fluctuation range threshold.

In the above solution, the breathing state of the patient includes at least one of assisted inhalation and assisted exhalation.

In the above solution, after recognizing the breathing state of the patient according to the change in the correlation data, the method further includes:

determining whether the recognized breathing state of the patient matches a current ventilation mode of the ventilation apparatus, and outputting a determination result.

In the above solution, the gas flow rate is a respiratory flow rate, and recognizing a breathing state of a patient according to a change in the correlation data includes:

determining that the breathing state of the patient is assisted inhalation when the correlation data is greater than zero; and determining that the breathing state of the patient is assisted exhalation when the correlation data is less than zero.

In the above solution, the gas flow rate is a gas supply flow rate, and recognizing a breathing state of a patient according to a change in the correlation data includes:

determining that the breathing state of the patient is assisted inhalation when the correlation data rises; and determining that the breathing state of the patient is assisted exhalation when the correlation data drops.

An embodiment of the disclosure provides a breathing recognition device, including:

an acquisition module for acquiring an airway pressure and a gas flow rate during mechanical ventilation, wherein the gas flow rate is a respiratory flow rate or a gas supply flow rate; and a processing module for determining correlation data corresponding to the airway pressure and the gas flow rate according to the airway pressure and the gas flow rate, and recognizing whether spontaneous breathing occurs according to a change in the correlation data.

In the above device, the processing module performs correlation calculation on the airway pressure and the gas flow rate according to a preset signal sampling rate and a preset sampling duration, so as to obtain the correlation data.

In the above device, the processing module respectively acquires a first sampled value corresponding to the airway pressure and a second sampled value corresponding to the gas flow rate within the preset sampling duration according to the preset signal sampling rate; and performs the correlation calculation on the first sampled value and the second sampled value to obtain the correlation data.

In the above device, the breathing state of the patient includes at least one of spontaneous inhalation and spontaneous exhalation, and after recognizing the breathing state of the patient according to the change in the correlation data, the processing module controls a ventilation apparatus to switch a ventilation mode according to the recognized breathing state of the patient.

In the above device, controlling the ventilation apparatus to switch a ventilation mode according to the recognized breathing state of the patient by the processing module includes:

triggering the ventilation apparatus to enter into an inhalation ventilation mode when the breathing state of the patient changes from spontaneous exhalation to spontaneous inhalation; and triggering the ventilation apparatus to enter into an exhalation ventilation mode when the breathing state of the patient changes from spontaneous inhalation to spontaneous exhalation.

In the above device, the gas flow rate is the respiratory flow rate, and recognizing a breathing state of a patient according to a change in the correlation data by the processing module includes:

determining that the breathing state of the patient is spontaneous inhalation when the correlation data is greater than a first preset threshold; and determining that the breathing state of the patient is spontaneous exhalation when the correlation data is less than a second preset threshold.

In the above device, the gas flow rate is the gas supply flow rate, and recognizing a breathing state of a patient according to a change in the correlation data by the processing module includes:

determining a parameter baseline corresponding to the correlation data;

determining that the breathing state of the patient is spontaneous exhalation when the correlation data is greater than the parameter baseline and a difference between the correlation data and the parameter baseline is greater than a third preset threshold; and determining that the breathing state of the patient is spontaneous inhalation when the correlation data is less than the parameter baseline and a difference between the correlation data and the parameter baseline is greater than a fourth preset threshold.

In the above device, determining a parameter baseline corresponding to the correlation data by the processing module includes:

calculating the correlation data in a first time period; and performing low-pass filtering on the correlation data in the first time period to obtain the parameter baseline.

In the above device, the breathing state of the patient includes asphyxia, and recognizing a breathing state of a patient according to a change in the correlation data by the processing module includes:

determining that the breathing state of the patient is asphyxia when the correlation data has a fluctuation range less than a preset fluctuation range threshold.

In the above device, the breathing state of the patient includes at least one of assisted inhalation and assisted exhalation.

In the above device, after recognizing the breathing state of the patient according to the change in the correlation data, the processing module further determines whether the recognized breathing state of the patient matches a current ventilation mode of the ventilation apparatus, and outputs a determination result.

In the above device, the gas flow rate is the respiratory flow rate, and recognizing a breathing state of a patient according to a change in the correlation data by the processing module includes:

determining that the breathing state of the patient is assisted inhalation when the correlation data is greater than zero; and determining that the breathing state of the patient is assisted exhalation when the correlation data is less than zero.

In the above device, the gas flow rate is the gas supply flow rate, and recognizing a breathing state of a patient according to a change in the correlation data by the processing module includes:

determining that the breathing state of the patient is assisted inhalation when the correlation data rises; and  determining that the breathing state of the patient is assisted exhalation when the correlation data drops.

An embodiment of the disclosure provides a ventilation apparatus including the above breathing recognition device, and including a gas source, a respiration pipeline, a display, and a controller, where  the gas source provides a gas during mechanical ventilation;

the respiration pipeline is connected to the gas source and provides an inspiratory path and an expiratory path during the mechanical ventilation;

the breathing recognition device is connected to the respiration pipeline and the controller;

the breathing recognition device recognizes a breathing state of a patient during the mechanical ventilation;

the controller is further connected to the gas source and controls a process of the mechanical ventilation; and  the display is connected to the controller and displays a respiratory waveform during the mechanical ventilation.

An embodiment of the disclosure provides a computer-readable storage medium, wherein the computer-readable storage medium stores a breathing recognition program, which is executable by a processor to implement the above breathing recognition method.

It can be seen that, in the technical solutions of the embodiment of the disclosure, an airway pressure and a gas flow rate are acquired during mechanical ventilation; correlation data corresponding to the airway pressure and the gas flow rate is determined according to the airway pressure and the gas flow rate; and a breathing state of a patient is recognized according to a change in the correlation data. That is to say, in the technical solution provided by the embodiment of the disclosure, the breathing state of the patient can be recognized according to the change in the correlation data of the airway pressure and the gas flow rate when the patient is mechanically ventilated, so as to effectively reduce the influence of interference signals on breathing recognition and improve the accuracy of breathing recognition.

DESCRIPTION OF THE PREFERRED EMBODIMENTS

In order to understand the features and technical contents of embodiments of the disclosure in more detail, the implementation of the embodiments of the disclosure will be described below in detail with reference to the accompanying drawings, and the accompanying drawings are for reference and illustration only, and are not intended to limit the embodiments of the disclosure.

Figure 6:
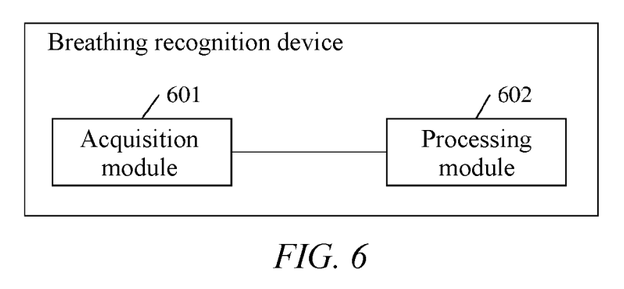
FIG. 6 is a schematic structural diagram of a breathing recognition device provided according to an embodiment of the disclosure.

An embodiment of the disclosure provides a breathing recognition method applicable to a ventilation apparatus. It should be noted that, in the embodiment of the disclosure, the breathing recognition method can be performed by a breathing recognition device. FIG. 6 is a schematic structural diagram of a breathing recognition device provided according to an embodiment of the disclosure. As shown in FIG. 6, the breathing recognition device includes an acquisition module 601 and a processing module 602. The breathing recognition method of the disclosure will be described below based on the breathing recognition device.

Figure 1:
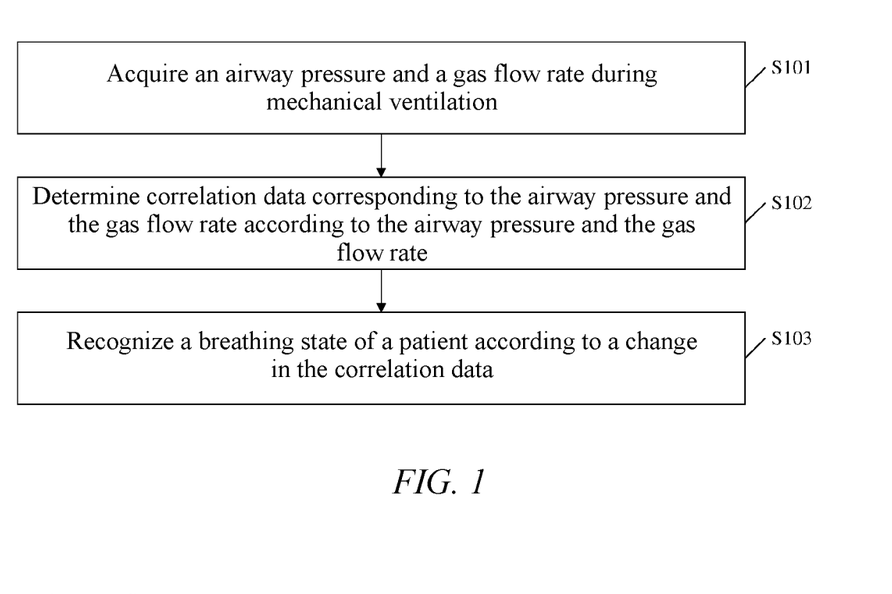
FIG. 1 is a schematic flow chart of a breathing recognition method provided according to an embodiment of the disclosure.

FIG. 1 is a schematic flow chart of the breathing recognition method provided according to an embodiment of the disclosure. As shown in FIG. 1, the breathing recognition method may mainly include the following steps.

At S101, an airway pressure and a gas flow rate are acquired during mechanical ventilation.

In the embodiment of the disclosure, the acquisition module 601 in the breathing recognition device may acquire the airway pressure and the gas flow rate in real time during the mechanical ventilation.

It should be noted that, in the embodiment of the disclosure, the gas flow rate can be a gas supply flow rate or a respiratory flow rate, and the specific gas flow rate is not limited in the embodiment of the disclosure.

It should be noted that, in the embodiment of the disclosure, the ventilation apparatus may be a medical apparatus with a ventilation function such as a ventilator and an anesthesia machine, and the ventilation apparatus may include the breathing recognition device. The specific ventilation apparatus is not limited in the embodiment of the disclosure.

It should be noted that, in the embodiment of the disclosure, the acquisition module 601 may acquire the airway pressure and the gas flow rate continuously, that is, from the beginning to the end of the mechanical ventilation, the acquisition module 601 is always acquiring the airway pressure and the gas flow rate.

It can be understood that, in the embodiment of the disclosure, the acquisition module 601 may be provided in a respiration pipeline of the ventilation apparatus, and the acquisition module 601 may include different sensors, such as a pressure sensor and a flow sensor, which are configured to acquire the airway pressure and the gas flow rate in real time. The specific method of acquiring the air airway pressure and the gas flow rate is not limited in the embodiment of the disclosure.

At S102, correlation data corresponding to the airway pressure and the gas flow rate is determined according to the airway pressure and the gas flow rate.

In the embodiment of the disclosure, after the acquisition module 601 in the breathing recognition device acquires the airway pressure and the gas flow rate, the processing module 602 may determine the correlation data corresponding to the airway pressure and the gas flow rate according to the airway pressure and the gas flow rate.

In the embodiment of the disclosure, the processing module 602 may determine the correlation data corresponding to the airway pressure and the gas flow rate according to the airway pressure and the gas flow rate by the following ways: performing correlation calculation on the airway pressure and the gas flow rate according to a preset signal sampling rate and a preset sampling duration, so as to obtain the correlation data.

It should be noted that, in the embodiment of the disclosure, a medical staff may determine a signal sampling rate and a sampling duration according to actual requirements, and set the determined signal sampling rate and sampling duration into the processing module 602. That is, the processing module 602 may pre-store the preset signal sampling rate and the preset sampling duration. The specific preset signal sampling rate and preset sampling duration are not limited in the embodiment of the disclosure.

In the embodiment of the disclosure, when the processing module 602 performs the correlation calculation on the airway pressure and the gas flow rate according to the preset signal sampling rate and the preset sampling duration so as to obtain the correlation data, the processing module 602 may specifically acquire a first sampled value corresponding to the airway pressure and a second sampled value corresponding to the gas flow rate respectively within the preset sampling duration according to the preset signal sampling rate, and perform the correlation calculation on the first sampled value and the second sampled value to obtain the correlation data.

It should be noted that, in the embodiment of the disclosure, the preset signal sampling rate may indicate the number of the airway pressure values and the number of the gas flow rate values that can be acquired within 1 s; and the preset sampling duration specifically defines a acquisition duration. That is, if the preset signal sampling rate is 1 KHZ and the preset sampling duration is 20 ms, the preset signal sampling rate of 1 KHZ indicates that 1000 sampled values corresponding to the airway pressure and 1000 sampled values corresponding to the gas flow rate can be acquired within 1 s; and the definition of the preset sampling duration of 20 ms indicates that the processing module 602 actually acquires the airway pressure and the gas flow rate for 20 ms through the acquisition module 601. Therefore, according to the preset signal sampling rate of 1 KHZ, it can be known that the processing module 602 can acquire 20 sampled values corresponding to the airway pressure and 20 sampled values corresponding to the gas flow rate through the acquisition module 601 within 20 ms, where the 20 sampled values acquired corresponding to the airway pressure are the first sampled values, and the 20 sampled values acquired corresponding to the gas flow rate are the second sampled values. After that, the correlation calculation may be performed on the first sampled values and the second sampled values, so as to obtain the correlation data corresponding to the airway pressure and the gas flow rate at a certain moment.

It can be understood that, in the embodiment of the disclosure, the number of the first sampled value and the number of the second sampled value are determined by the preset signal sampling rate and the preset sampling duration. There may be a plurality of the first sampled values and a plurality of the second sampled values, while the number of the first sampled value and the number of the second sampled value are the same, and the first sampled values and the second sampled values are in one-to-one correspondence. That is, when one first sampled value is acquired at a certain moment within the preset sampling duration, one corresponding second sampled value will be acquired at the same time.

As an example, in the embodiment of the disclosure, the preset signal sampling rate is 1 KHZ, the preset sampling duration is 20 ms, and the processing module 602 may calculate the correlation data of the airway pressure and the gas flow rate according to Equation 1:

$$\mathrm{Corr}(k) = \sum_{i=k-19}^{k} \mathrm{Flow}\ (i) * \mathrm{Pressure}\ (i)$$

wherein Corr(k) represents the correlation data of the airway pressure and the gas flow rate at a moment k, Flow (i) represents the gas flow rate at a moment i, and Pressure (i) represents the airway pressure at a moment i.

It can be understood that, in the embodiment of the disclosure, when the preset signal sampling rate is 1 KHZ and the preset sampling duration is 20 ms, the processing module 602 actually acquires 20 first sampled values corresponding to the airway pressure, and also acquires 20 second sampled values corresponding to the gas flow rate. Therefore, when the correlation data of the airway pressure and the gas flow rate at a certain moment is being calculated, for example, at moment k, the airway pressure and the gas flow rate at a moment k, and the airway pressures and the gas flow rates at the previous 19 moments before the moment k may be substituted into Equation 1 for calculation to obtain the correlation data of the airway pressure and the gas flow rate at the moment k.

Figure 2A:
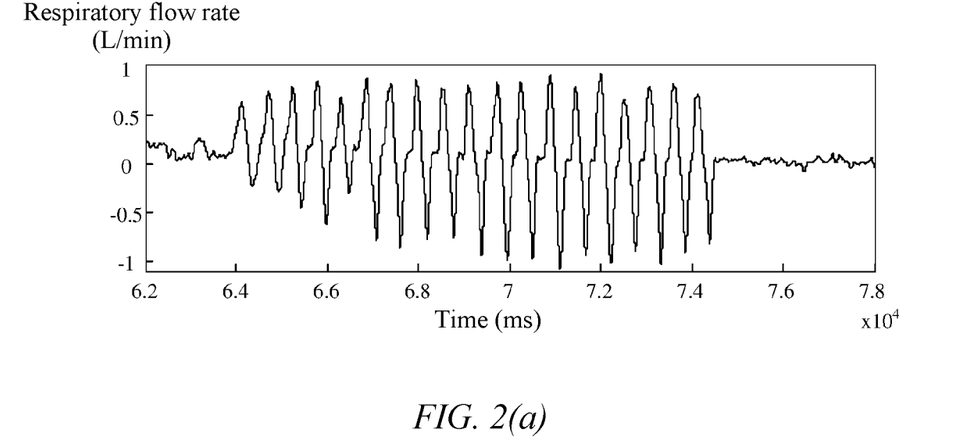
FIG. 2(a) is an exemplary schematic waveform diagram of a respiratory flow rate provided according to an embodiment of the disclosure.
Figure 2B:
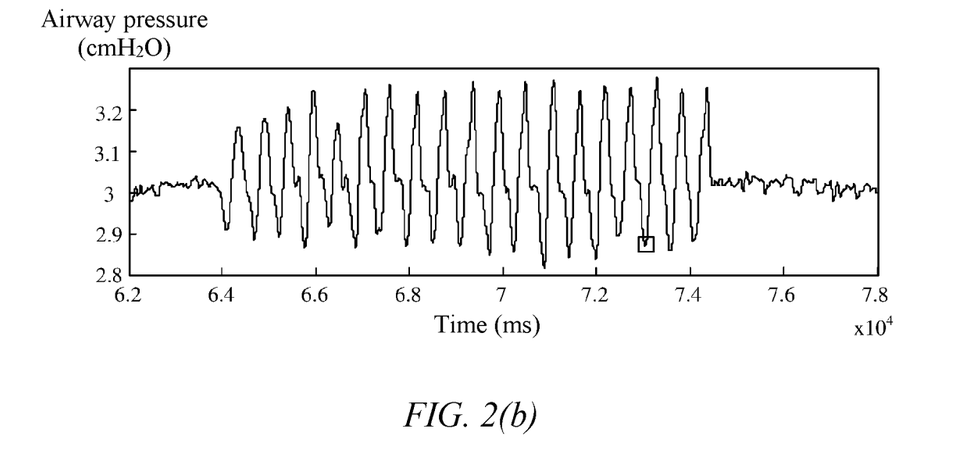
FIG. 2(b) is a first exemplary schematic waveform diagram of an airway pressure provided according to an embodiment of the disclosure.
Figure 2C:
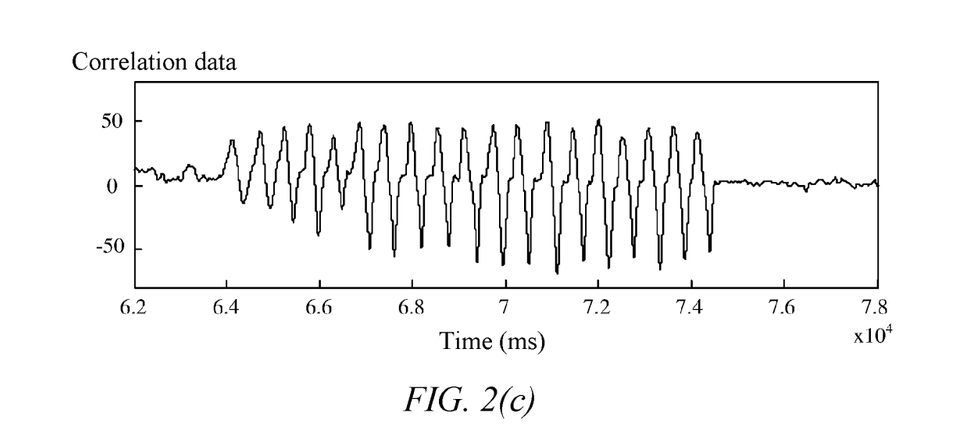
FIG. 2(c) is a first exemplary schematic waveform diagram of correlation data provided according to an embodiment of the disclosure.

FIG. 2(*a*) is an exemplary schematic waveform diagram of a respiratory flow rate provided according to an embodiment of the disclosure. FIG. 2(*b*) is a first exemplary schematic waveform diagram of an airway pressure provided according to an embodiment of the disclosure. FIG. 2(*c*) is a first exemplary schematic waveform diagram of correlation data provided according to an embodiment of the disclosure. As shown in FIG. 2(*a*), the gas flow rate is the respiratory flow rate. If the preset signal sampling rate is 1 KHZ and the preset sampling duration is 20 ms, the processing module 602 performs the correlation calculation on the respiratory flow rate shown in FIG. 2(*a*) and the airway pressure shown in FIG. 2(*b*) to obtain the correlation data shown in FIG. 2(*c*).

Figure 3A:
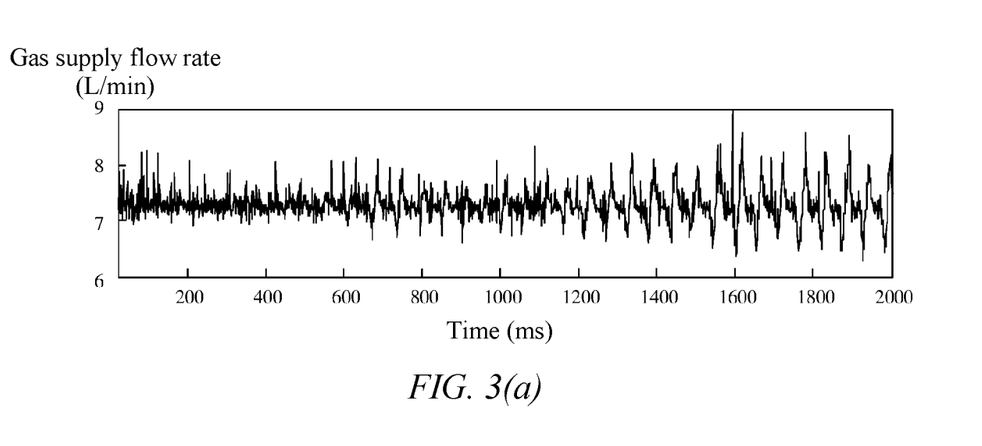
FIG. 3(a) is an exemplary schematic waveform diagram of a gas supply flow rate provided according to an embodiment of the disclosure.
Figure 3B:
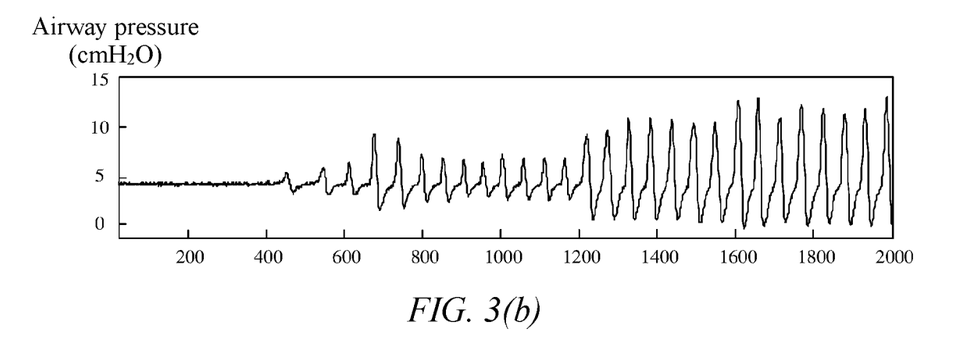
FIG. 3(b) is a second exemplary schematic waveform diagram of an airway pressure provided according to an embodiment of the disclosure.
Figure 3C:
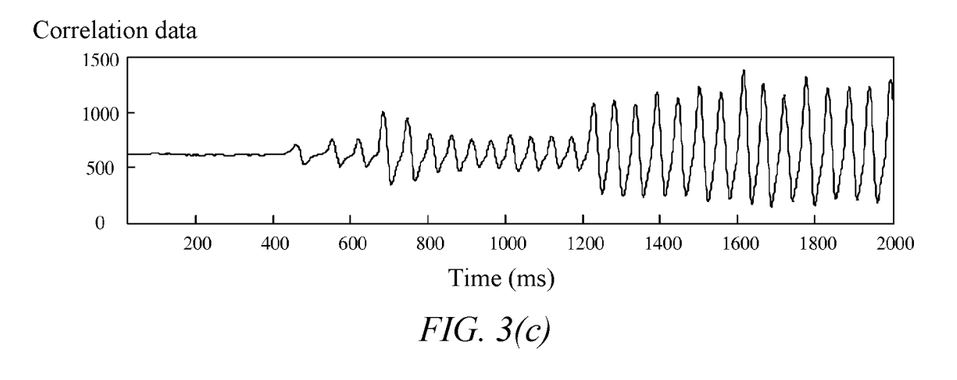
FIG. 3(c) is a second exemplary schematic waveform diagram of correlation data provided according to an embodiment of the disclosure.

FIG. 3(a) is an exemplary schematic waveform diagram of a gas supply flow rate provided according to an embodiment of the disclosure. FIG. 3(b) is a second exemplary schematic waveform diagram of an airway pressure provided according to an embodiment of the disclosure. FIG. 3(c) is a second exemplary schematic waveform diagram of correlation data provided according to an embodiment of the disclosure. As shown in FIG. 3(a), the gas flow rate is the gas supply flow rate. If the preset signal sampling rate is 1 KHZ and the preset sampling duration is 20 ms, the processing module 602 performs the correlation calculation on the gas supply flow rate shown in FIG. 3(a) and the airway pressure shown in FIG. 3(b) to obtain the correlation data shown in FIG. 3(c).

Figure 4A:
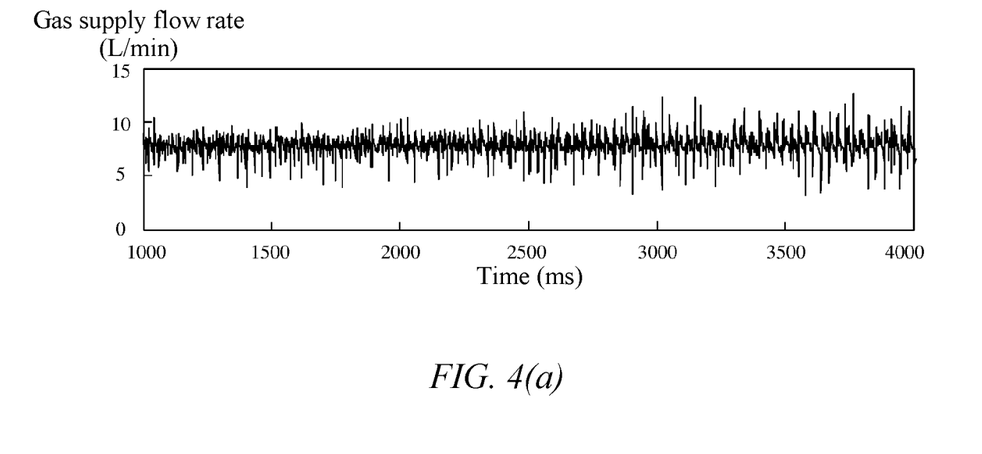
FIG. 4(a) is an exemplary schematic waveform diagram of a gas supply flow rate provided according to an embodiment of the disclosure with water being accumulated in a pipeline.
Figure 4B:
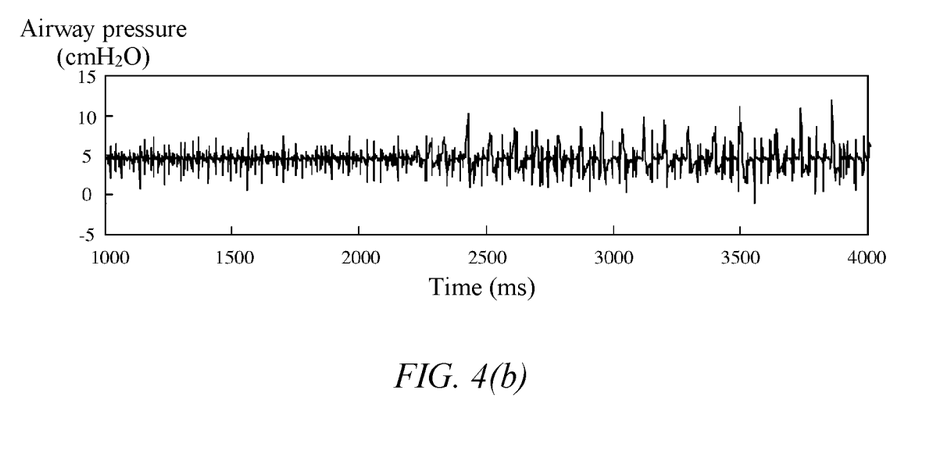
FIG. 4(b) is an exemplary schematic waveform diagram of an airway pressure provided according to an embodiment of the disclosure with water being accumulated in a pipeline.
Figure 4C:
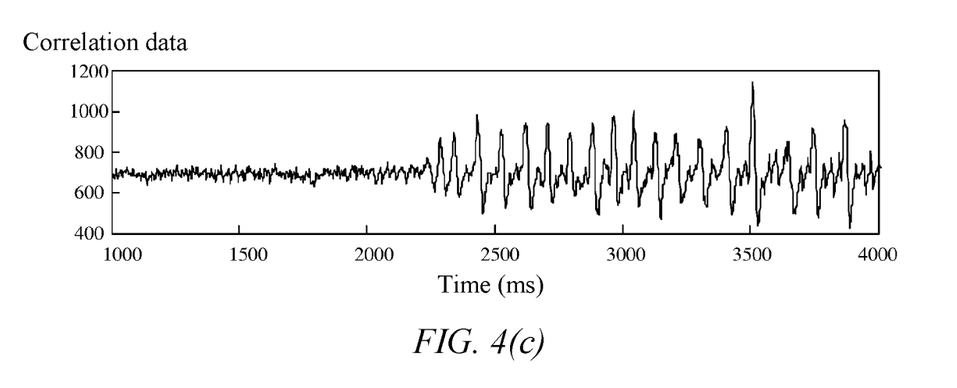
FIG. 4(c) is an exemplary schematic waveform diagram of correlation data provided according to an embodiment of the disclosure with water being accumulated in a pipeline.

FIG. 4(a) is an exemplary schematic waveform diagram of a gas supply flow rate provided according to an embodiment of the disclosure with water being accumulated in a pipeline. FIG. 4(b) is an exemplary schematic waveform diagram of an airway pressure provided according to an embodiment of the disclosure with water being accumulated in a pipeline. FIG. 4(c) is an exemplary schematic waveform diagram of correlation data provided according to an embodiment of the disclosure with water being accumulated in a pipeline. When water is accumulated in a pipeline of the ventilation apparatus, the gas flow causes the water accumulated in the pipeline to flow, thereby causing frequent fluctuations in the gas supply flow rate and the airway pressure. As shown in FIGS. 4(a) and 4(b), these fluctuations are superimposed on the waveforms of the gas supply flow rate and the airway pressure, which will make it difficult to recognize the breathing state of the patient. However, when the processing module 602 performs the correlation calculation on the gas supply flow rate in FIG. 4(a) and the airway pressure shown in FIG. 4(b) according to the above correlation equation, the waveform diagram shown in FIG. 4(c) can be obtained, and the breathing state of the patient can be clearly recognized.

It can be understood that in the prior art, breathing recognition is usually performed based on only one of the airway pressure and the gas flow rate, and the changes in the airway pressure and the gas flow rate are usually not clear enough, and are easily interfered with by other factors, so that the breathing cannot be accurately recognized. In the embodiment of the disclosure, considering that the changes in the airway pressure and the gas flow rate are opposite, correlation data corresponding to the airway pressure and the gas flow rate is calculated. According to FIGS. 2(c), 3(c) and 4(c) above, it can be clearly seen that the correlation data can clearly represent the fluctuation of the patient's breathing; that is, the correlation data can amplify small respiratory fluctuations, and thus the breathing state of the patient can be more accurately recognized.

At S103, a breathing state of a patient is recognized according to a change in the correlation data.

In the embodiment of the disclosure, after determining the correlation data corresponding to the airway pressure and the gas flow rate, the processing module 602 in the breathing recognition device may recognize the breathing state of the patient according to the change in the correlation data.

It should be noted that, in the embodiment of the disclosure, the breathing state of the patient includes: spontaneous inhalation, spontaneous exhalation, asphyxia, assisted inhalation and assisted exhalation, where the processing module 602 may recognize the specific breathing state of the patient according to the change in the correlation data.

Specifically, in the embodiment of the disclosure, when the gas flow rate is the respiratory flow rate, the step of recognizing the breathing state of the patient according to the change in the correlation data by the processing module 602 may include: determining that the breathing state of the patient is spontaneous inhalation when the correlation data is greater than a first preset threshold; and determining that the breathing state of the patient is spontaneous exhalation when the correlation data is less than a second preset threshold.

It should be noted that in the embodiment of the disclosure, the processing module 602 stores the first preset threshold and the second preset threshold, and the first preset threshold is preset to be greater than the second preset threshold. The specific first preset threshold and the second preset threshold are not limited in the embodiment of the disclosure.

As an example, in the embodiment of the disclosure, the gas flow rate is the respiratory flow rate. Accordingly, the processing module 602 may determine the correlation data corresponding to the respiratory flow rate and the airway pressure in real time. The first preset threshold is A1, and the second preset threshold is A2. If the correlation data corresponding to the respiratory flow rate and the airway pressure is greater than A1, it is determined that the breathing state of the patient is spontaneous inhalation. If the correlation data corresponding to the respiratory flow rate and the airway pressure is less than A2, it is determined that the breathing state of the patient is spontaneous exhalation.

It can be understood that, in the embodiment of the disclosure, during the mechanical ventilation by the ventilation apparatus, if the patient inhales spontaneously, the airway pressure will drop. At this time, in order to meet the patient's inhalation needs, the gas supply flow rate or the respiratory flow rate increases. That is, the gas flow rate and the airway pressure have opposite phases. Similarly, if the patient exhales spontaneously, the gas flow rate and the airway pressure also have opposite phases. Therefore, the spontaneous inhalation and the spontaneous exhalation can be clearly recognized by using the change in the correlation data corresponding to the gas flow rate and the airway pressure.

It should be noted that, in the embodiment of the disclosure, under normal circumstances, the respiratory flow rate during the inhalation phase is greater than zero, and the respiratory flow rate during the expiration phase is less than zero, while the airway pressure is greater than zero. Therefore, when determining spontaneous inhalation and spontaneous exhalation according to the correlation data corresponding to the respiratory flow rate and the airway pressure, the processing module 602 may determine the breathing state as spontaneous inhalation when the correlation data is greater than a certain threshold, namely the first preset threshold, and determine the breathing state as spontaneous exhalation when the correlation data is less than a certain threshold, namely the second preset threshold.

Specifically, in the embodiment of the disclosure, if the gas flow rate is the gas supply flow rate, the step of recognizing the breathing state of the patient according to the change in the correlation data by the processing module 602 may include: determining a parameter baseline corresponding to the correlation data; determining that the breathing state of the patient is spontaneous exhalation when the correlation data is greater than the parameter baseline and a difference between the correlation data and the parameter baseline is greater than a third preset threshold; and determining that the breathing state of the patient is spontaneous inhalation when the correlation data is less than the parameter baseline and a difference between the correlation data and the parameter baseline is greater than a fourth preset threshold.

It should be noted that, in the embodiment of the disclosure, the processing module 602 stores the third preset threshold and the fourth preset threshold. The specific third preset threshold and fourth preset threshold are not limited in the embodiment of the disclosure.

It should be noted that, in the embodiment of the disclosure, if the gas flow rate is the gas supply flow rate, when the processing module 602 needs to first determine the parameter baseline corresponding to the correlation data which corresponds to the gas flow rate and the airway pressure, the processing module may calculate the correlation data in a first time period; and perform low-pass filtering on the correlation data in the first time period to obtain the parameter baseline.

It should be noted that, in the embodiment of the disclosure, the first time period may be a relatively long time period preset in the processing module 602 by a medical staff, and the processing module 602 may calculate the correlation data corresponding to the gas supply flow rate and the airway pressure in the first time period, and perform the low-pass filtering on the correlation data in this time period to filter out a fluctuation range, so as obtain a reference baseline which is the parameter baseline. The specific first time period is not limited in the embodiment of the disclosure.

Figure 5:
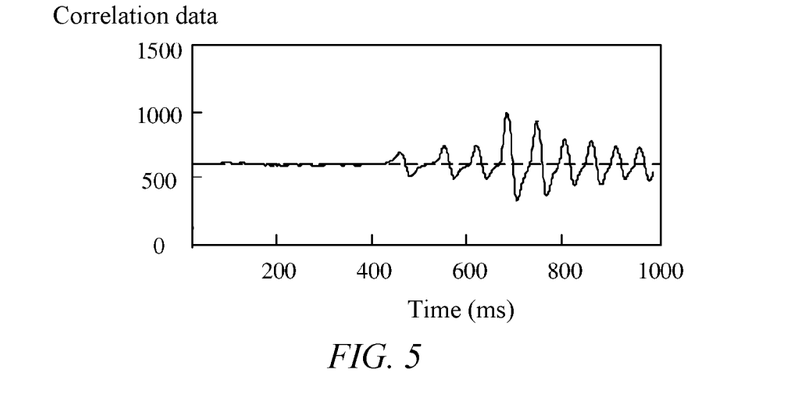
FIG. 5 is an exemplary schematic diagram of a parameter baseline provided according to an embodiment of the disclosure.

FIG. 5 is an exemplary schematic diagram of a parameter baseline provided according to an embodiment of the disclosure. As shown in FIG. 5, the first time period is 1000 ms, and a solid line shows the correlation data corresponding to the gas supply flow rate and the airway pressure within 1000 ms. After low-pass filtering is performed on the correlation data, the parameter baseline shown in a dotted portion can be obtained.

It should be noted that, in the embodiment of the disclosure, the processing module 602 may specifically further calculate a mean of the correlation data corresponding to the gas supply flow rate and the airway pressure in the first time period, where the mean is determined as the parameter baseline.

As an example, in the embodiment of the disclosure, the gas flow rate is the gas supply flow rate; after determining that the parameter baseline is shown by the dotted line in FIG. 5, the processing module 602 can determine the correlation data corresponding to the gas supply flow rate and the airway pressure in real time. The third preset threshold is A3, and the fourth preset threshold is A4. When the correlation data corresponding to the gas supply flow rate and the airway pressure is greater than the parameter baseline and the difference between the two is greater than A3, it is determined that the breathing state of the patient is spontaneous exhalation; and when the correlation data corresponding to the gas supply flow rate and the airway pressure is less than the parameter baseline and the difference between the two is greater than A4, it is determined that the breathing state of the patient is spontaneous inhalation.

It should be noted that, in the embodiment of the disclosure, under normal circumstances, the gas supply flow rate is greater than zero, and the airway pressure is also greater than zero. In fact, the parameter baseline is greater than zero. According to the relationship between the gas supply flow rate and the airway pressure, it can be seen that when the correlation data is less than the parameter baseline, it is the inhalation phase, and when the correlation data is greater than the parameter baseline, it is the exhalation phase.

Therefore, when determining spontaneous inhalation and spontaneous exhalation according to the correlation data corresponding to the gas supply flow rate and the airway pressure, the processing module 602 may determine the breathing state as spontaneous exhalation when the correlation data is greater than the parameter baseline by a certain threshold, namely the third preset threshold, and determine the breathing state as spontaneous inhalation when the correlation data is less than the parameter baseline by a certain threshold, namely the fourth preset threshold.

It should be noted that, in the embodiment of the disclosure, after recognizing that the breathing state of the patient is spontaneous inhalation or spontaneous exhalation, the processing module 602 may further control the ventilation apparatus to switch a ventilation mode according to the recognized breathing state of the patient.

Specifically, in the embodiment of the disclosure, when the processing module 602 performs the step of controlling the ventilation apparatus to switch the ventilation mode according to the recognized breathing state of the patient, the processing module 602 may trigger the ventilation apparatus to enter into an inhalation ventilation mode when the breathing state of the patient changes from spontaneous exhalation to spontaneous inhalation; and trigger the ventilation apparatus to enter into an exhalation ventilation mode when the breathing state of the patient changes from spontaneous inhalation to spontaneous exhalation.

It should be noted that, in the embodiment of the disclosure, when the processing module 602 triggers the ventilation apparatus to enter into the inhalation ventilation mode or the exhalation ventilation mode, the processing module 602 may output a corresponding control signal to a controller of the ventilation apparatus, and the controller may control to enter into the inhalation ventilation mode or the exhalation ventilation mode according to the control signal. The specific trigger way is not limited in the embodiment of the disclosure.

Specifically, in the embodiment of the disclosure, the breathing state of the patient includes asphyxia, the step of recognizing the breathing state of the patient according to the change in the correlation data by the processing module 602 may include: determining that the breathing state of the patient is asphyxia when the correlation data has a fluctuation range less than a preset fluctuation range threshold.

It should be noted that, in the embodiment of the disclosure, the processing module 602 stores the preset fluctuation range, and the medical staff can adjust the preset fluctuation range according to actual requirements. The specific preset fluctuation range is not limited in the embodiment of the disclosure.

It can be understood that, in the embodiment of the disclosure, if the breathing state of the patient is asphyxia, that is, the patient cannot breathe normally, the gas flow rate and the airway pressure remain basically unchanged, and the correlation data basically does not fluctuate, so that it can be recognized that the patient is subjected to asphyxia.

It should be noted that, in the embodiment of the disclosure, the correlation data used by the processing module 602 to recognize the asphyxia may be the correlation data corresponding to the respiratory flow rate and the airway pressure, or may be the correlation data corresponding to the gas supply flow rate and the airway pressure. As long as the fluctuation range of the correlation is less than the preset fluctuation range threshold, it can be recognized that the breathing state of the patient is asphyxia.

Specifically, in the embodiment of the disclosure, the breathing state of the patient includes at least one of assisted inhalation and assisted exhalation. When the gas flow rate is the respiratory flow rate and the processing module 602 recognizes the breathing state of the patient according to the change in the correlation data, the processing module 602 may determine that the breathing state of the patient is assisted inhalation when the correlation data is greater than zero; and determine that the breathing state of the patient is assisted exhalation when the correlation data is less than zero.

It should be noted that, in the embodiment of the disclosure, under normal circumstances, the respiratory flow rate during the inhalation phase is greater than zero, and the respiratory flow rate during the expiration phase is less than zero, while the airway pressure is greater than zero. Therefore, when the ventilation apparatus assists the patient to inhale, the processing module 602 may determine that the breathing state of the patient is assisted inhalation when the correlation data corresponding to the respiratory flow rate and the airway pressure is greater than zero. When the ventilation apparatus assists the patient to exhale, the processing module 602 may determine that the breathing state of the patient is assisted exhalation when the correlation corresponding to the respiratory flow rate and the airway pressure is less than zero.

Specifically, in the embodiment of the disclosure, the breathing state of the patient includes at least one of assisted inhalation and assisted exhalation. When the gas flow rate is the gas supply flow rate and the processing module 602 recognizes the breathing state of the patient according to the change in the correlation data, the processing module 602 may determine that the breathing state of the patient is assisted inhalation when the correlation data rises; and determine that the breathing state of the patient is assisted exhalation when the correlation data drops.

It should be noted that, in the embodiment of the disclosure, under normal circumstances, the gas supply flow rate is greater than zero, and the airway pressure is also greater than zero. When the ventilation apparatus assists the patient in inhaling, the gas supply flow rate may remain unchanged, while the airway pressure will gradually increase. Therefore, the correlation data corresponding to the gas supply flow rate and the airway pressure will rise, and the breathing state of the patient can be determined as assisted inhalation. When the ventilation apparatus assists the patient in exhaling, the gas supply flow rate will decrease and the airway pressure will also decrease. Therefore, the correlation data corresponding to the gas supply flow rate and the airway pressure will drop, and the breathing state of the patient can be determined as assisted exhalation.

It should be noted that, in the embodiment of the disclosure, after recognizing that the breathing state of the patient is assisted inhalation or assisted exhalation according to the change in the correlation data, the processing module 602 may further determine whether the recognized breathing state of the patient matches a current ventilation mode of the ventilation apparatus and further output a determination result.

As an example, in an embodiment of the disclosure, the processing module 602 recognizes that the breathing state of the patient is assisted inhalation. In this case, if the current ventilation mode of the ventilation apparatus is the assisted inhalation mode, the breathing state and the current ventilation mode match, and the processing module 602 may output a determination result: 1, to represent the determination result of matching; otherwise, if the current ventilation mode of the ventilation apparatus is the assisted exhalation mode, the breathing state and the current ventilation mode do not match, and the processing module 602 may output a determination result: 0, to represent the determination result of mismatch.

As an example, in an embodiment of the disclosure, the processing module 602 recognizes that the breathing state of the patient is assisted inhalation. In this case, if the current ventilation mode of the ventilation apparatus is the assisted inhalation mode, that is, the breathing state and the current ventilation mode match, the processing module 602 may output a first control instruction to the controller of the ventilation apparatus, and the controller controls a corresponding indicator light to display green according to the first control instruction, which is used to represent the determination result of matching; otherwise, if the current ventilation mode of the ventilation apparatus is the assisted exhalation mode, that is, the breathing state and the current ventilation mode do not match, the processing module 602 may output a second control instruction to the controller, and the controller controls a corresponding indicator light to display red according to the second control instruction, which is used to represent the determination result of mismatch.

It can be understood that, in the embodiment of the disclosure, the processing module 602 may recognize that the breathing state of the patient is assisted inhalation, while the current ventilation mode of the ventilation apparatus is assisted exhalation; that is, the breathing state and the current ventilation mode do not match with each other. In this case, it may indicate that there is a problem with the ventilation mode, or some problems have occurred during the ventilation process, and the medical staff can perform corresponding treatment and maintenance based on this determination result.

In the breathing recognition method provided in the embodiments of the disclosure, the airway pressure and the gas flow rate are acquired during mechanical ventilation; the correlation data corresponding to the airway pressure and the gas flow rate is determined according to the airway pressure and the gas flow rate; and the breathing state of the patient is recognized according to the change in the correlation data. That is to say, in the technical solution provided by the embodiments of the disclosure, the breathing state of the patient can be recognized according to the change in the correlation data of the airway pressure and the gas flow rate when the patient is mechanically ventilated, so as to effectively reduce the influence of interference signals on breathing recognition and improve the accuracy of breathing recognition.

Another embodiment of the disclosure provides a breathing recognition device. FIG. 6 is a schematic structural diagram of a breathing recognition device provided according to an embodiment of the disclosure. As shown in FIG. 6, the device includes an acquisition module 601 and a processing module 602.

The acquisition module 601 is configured for acquiring an airway pressure and a gas flow rate during mechanical ventilation, where the gas flow rate is a respiratory flow rate or a gas supply flow rate.

The processing module 602 is configured for determining correlation data corresponding to the airway pressure and the gas flow rate according to the airway pressure and the gas flow rate, and recognizing whether spontaneous breathing occurs according to a change in the correlation data.

Optionally, the processing module 602 performs correlation calculation on the airway pressure and the gas flow rate according to a preset signal sampling rate and a preset sampling duration, so as to obtain the correlation data.

Optionally, the processing module 602 respectively acquires a first sampled value corresponding to the airway pressure and a second sampled value corresponding to the gas flow rate within the preset sampling duration according to the preset signal sampling rate; and performs correlation calculation on the first sampled value and the second sampled value to obtain the correlation data.

Optionally, the breathing state of the patient includes at least one of spontaneous inhalation and spontaneous exhalation.

After recognizing the breathing state of the patient according to the change in the correlation data, the processing module 602 controls the ventilation apparatus to switch a ventilation mode according to the recognized breathing state of the patient.

Optionally, the step of controlling the ventilation apparatus to switch the ventilation mode according to the recognized breathing state of the patient by the processing module 602 includes:

triggering the ventilation apparatus to enter into an inhalation ventilation mode if the breathing state of the patient changes from spontaneous exhalation to spontaneous inhalation; and triggering the ventilation apparatus to enter into an exhalation ventilation mode if the breathing state of the patient changes from spontaneous inhalation to spontaneous exhalation.

Optionally, the gas flow rate is the respiratory flow rate, and the step of recognizing the breathing state of the patient according to the change in the correlation data by the processing module 602 includes:

determining that the breathing state of the patient is spontaneous inhalation when the correlation data is greater than a first preset threshold; and determining that the breathing state of the patient is spontaneous exhalation when the correlation data is less than a second preset threshold.

Optionally, the gas flow rate is the gas supply flow rate, and the step of recognizing the breathing state of the patient according to the change in the correlation data by the processing module 602 includes:

determining a parameter baseline corresponding to the correlation data;

determining that the breathing state of the patient is spontaneous exhalation when the correlation data is greater than the parameter baseline and a difference between the correlation data and the parameter baseline is greater than a third preset threshold; and determining that the breathing state of the patient is spontaneous inhalation when the correlation data is less than the parameter baseline and a difference between the correlation data and the parameter baseline is greater than a fourth preset threshold.

Optionally, the step of determining the parameter baseline corresponding to the correlation data by the processing module 602 includes:

calculating the correlation data in a first time period; and
performing low-pass filtering on the correlation data in the first time period to obtain the parameter baseline.

Optionally, the breathing state of the patient includes asphyxia, the step of recognizing the breathing state of the patient according to the change in the correlation data by the processing module 602 includes:

determining that the breathing state of the patient is asphyxia when the correlation data has a fluctuation range less than a preset fluctuation range threshold.

Optionally, the breathing state of the patient includes at least one of assisted inhalation and assisted exhalation.

Optionally, after recognizing the breathing state of the patient according to the change in the correlation data, the processing module 602 determines whether the recognized breathing state of the patient matches the current ventilation mode of the ventilation apparatus, and outputs a determination result.

Optionally, the gas flow rate is the respiratory flow rate, and the step of recognizing the breathing state of the patient according to the change in the correlation data by the processing module 602 includes:

determining that the breathing state of the patient is assisted inhalation when the correlation data is greater than zero; and determining that the breathing state of the patient is assisted exhalation when the correlation data is less than zero.

Optionally, the gas flow rate is the gas supply flow rate, and the step of recognizing the breathing state of the patient according to the change in the correlation data by the processing module 602 includes:

determining that the breathing state of the patient is assisted inhalation when the correlation data rises; and determining that the breathing state of the patient is assisted exhalation when the correlation data drops.

In the breathing recognition device provided in an embodiment of the disclosure, the airway pressure and the gas flow rate are acquired during mechanical ventilation; the correlation data corresponding to the airway pressure and the gas flow rate is determined according to the airway pressure and the gas flow rate; and the breathing state of the patient is recognized according to the change in the correlation data. That is to say, the breathing recognition device provided by the embodiment of the disclosure can recognize the breathing state of the patient according to the change in the correlation data of the airway pressure and the gas flow rate when the patient is mechanically ventilated, so as to effectively reduce the influence of interference signals on breathing recognition and improve the accuracy of breathing recognition.

Figure 7:
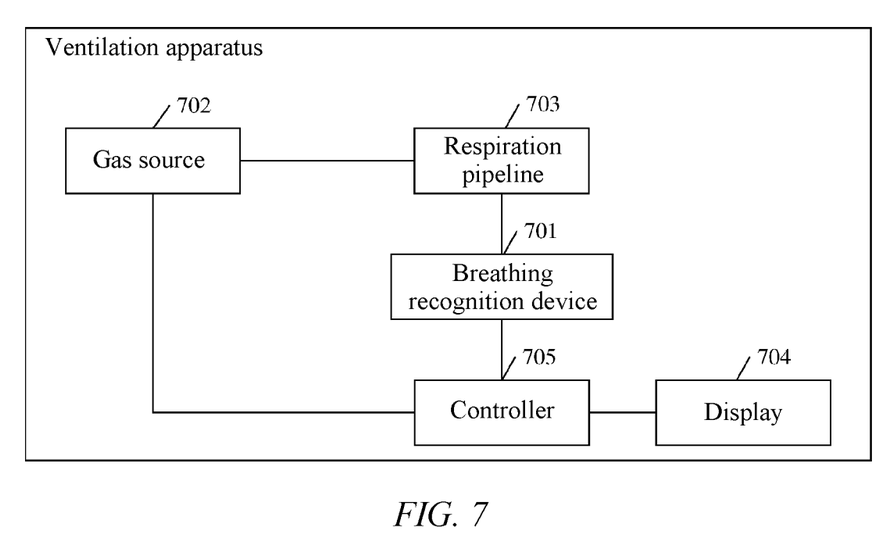
FIG. 7 is a schematic structural diagram of a ventilation apparatus provided according to an embodiment of the disclosure.

An embodiment of the disclosure provides a ventilation apparatus. FIG. 7 is a schematic structural diagram of a ventilation apparatus provided according to an embodiment of the disclosure. As shown in FIG. 7, the ventilation apparatus includes the breathing recognition device 701 described above, and further includes a gas source 702, a respiration pipeline 703, a displayer 704, and a controller 705.

The gas source 702 provides a gas during mechanical ventilation.

The respiration pipeline 703 is connected to the gas source 702 and provides an inspiratory path and an expiratory path during the mechanical ventilation.

The breathing recognition device 701 is connected to the respiration pipeline 703 and the controller 705, and is configured to recognize a breathing state of a patient during the mechanical ventilation.

The controller 705 is further connected to the gas source 702 and controls the process of the mechanical ventilation.

The displayer 704 is connected to the controller 705 and displays a respiratory waveform during the mechanical ventilation.

An embodiment of the disclosure provides a computer-readable storage medium, wherein the computer-readable storage medium stores a breathing recognition program, which is executable by a processor to implement the above breathing recognition method. The computer-readable storage medium may be a volatile memory, such as a random-access memory (RAM), or a non-volatile memory, such as a read-only memory (ROM), a flash memory, a hard disk drive (HDD) or a solid-state drive (SSD); or a respective apparatus including one or any combination of the above memories, such as a mobile phone, a computer, a tablet, and a personal digital assistant.

Those skilled in the art should understand that the embodiments of the disclosure may be provided as a method, a system, or a computer program product. Therefore, the disclosure may take the form of hardware embodiments, software embodiments, or embodiments with a combination of software and hardware. Moreover, the disclosure may take the form of a computer program product that is implemented on one or more computer-usable storage media (including but not limited to a disk memory and an optical memory, etc.) that include computer-usable program codes.

The disclosure is described with reference to flow charts and/or block diagrams of the methods, apparatuses (systems), and computer program products according to the embodiments of the disclosure. It should be understood that each procedure and/or block in the flow charts and/or block diagrams, and combinations of the procedures and/or blocks in the flow charts and/or block diagrams may be implemented by computer program instructions. These computer program instructions may be provided to a processor of a general-purpose computer, a special-purpose computer, an embedded processor or other programmable signal processing apparatuses to create a machine, such that the instructions executed by the processor of the computer or other programmable signal processing apparatuses create a device for implementing functions specified in one or more procedures in the flow charts and/or one or more blocks in the block diagrams.

These computer program instructions may also be stored in a computer-readable memory that may direct the computer or other programmable signal processing apparatus to operate in a specific manner, such that the instructions stored in the computer-readable memory create an article of manufacture including an instruction device, and the instruction device implements the functions specified in one or more procedures of the flow charts and/or one or more blocks of the block diagrams.

These computer program instructions can also be loaded onto the computer or other programmable signal processing apparatuses, such that a series of operation steps are executed on the computer or other programmable apparatuses to perform computer-implemented processing, and thus the instructions executed on the computer or other programmable apparatuses provide steps for implementing the functions specified in one or more procedures of the flow charts and/or one or more blocks of the block diagrams.

The above description is only preferred embodiments of the disclosure, and is not intended to limit the scope of protection of the disclosure.

What is claimed is:

1. A breathing recognition method, which is applicable to a ventilation apparatus, the method comprising:
acquiring an airway pressure and a gas flow rate during mechanical ventilation;
calculating correlation data indicating a correlation between the airway pressure and the gas flow rate according to the airway pressure and the gas flow rate using a correlation equation;
recognizing a breathing state of a patient according to a change in the correlation data; and
controlling the ventilation apparatus to switch a ventilation mode according to the recognized breathing state of the patient;
wherein the breathing state of the patient comprises at least one of spontaneous inhalation and spontaneous exhalation; when the gas flow rate is a gas supply flow rate, recognizing the breathing state of the patient according to the change in the correlation data comprises:
determining a parameter baseline corresponding to the correlation data;
determining that the breathing state of the patient is spontaneous exhalation when the correlation data is greater than the parameter baseline and a difference between the correlation data and the parameter baseline is greater than a third preset threshold; and
determining that the breathing state of the patient is spontaneous inhalation when the correlation data is less than the parameter baseline and a difference between the correlation data and the parameter baseline is greater than a fourth preset threshold.

2. The method of claim 1, wherein calculating the correlation data indicating the correlation corresponding to the airway pressure and the gas flow rate according to the airway pressure and the gas flow rate using the correlation equation comprises:
performing correlation calculation between the airway pressure and the gas flow rate using the correlation equation and samples obtained according to a preset signal sampling rate within a preset sampling duration, so as to obtain the correlation data.

3. The method of claim 2, wherein performing correlation calculation between the airway pressure and the gas flow rate using the correlation equation and the samples obtained according to the preset signal sampling rate within the preset sampling duration so as to obtain the correlation data comprises:
acquiring a first sampled value corresponding to the airway pressure and a second sampled value corresponding to the gas flow rate respectively within the preset sampling duration according to the preset signal sampling rate; and
performing the correlation calculation between the first sampled value and the second sampled value to obtain the correlation data.

4. The method of claim 1, wherein controlling the ventilation apparatus to switch the ventilation mode according to the recognized breathing state of the patient comprises:
triggering the ventilation apparatus to enter into an inhalation ventilation mode when the breathing state of the patient changes from spontaneous exhalation to spontaneous inhalation; and
triggering the ventilation apparatus to enter into an exhalation ventilation mode when the breathing state of the patient changes from spontaneous inhalation to spontaneous exhalation.

5. The method of claim 1, wherein when the gas flow rate is a respiratory flow rate, recognizing the breathing state of the patient according to the change in the correlation data comprises:
determining that the breathing state of the patient is spontaneous inhalation when the correlation data is greater than a first preset threshold; and
determining that the breathing state of the patient is spontaneous exhalation when the correlation data is less than a second preset threshold.

6. The method of claim 1, wherein determining the parameter baseline corresponding to the correlation data comprises:
calculating the correlation data in a first time period; and
performing low-pass filtering on the correlation data in the first time period to obtain the parameter baseline.

7. The method of claim 1, wherein the breathing state of the patient comprises asphyxia, and recognizing the breathing state of the patient according to the change in the correlation data comprises:
determining that the breathing state of the patient is asphyxia when the correlation data has a fluctuation range less than a preset fluctuation range threshold.

8. The method of claim 1, wherein
the breathing state of the patient comprises at least one of assisted inhalation and assisted exhalation, and after recognizing the breathing state of the patient according to the change in the correlation data, the method further comprises:
controlling the ventilation apparatus to have maintenance according to the recognized breathing state of the patient.

9. The method of claim 1, wherein the breathing state of the patient comprises at least one of assisted inhalation and assisted exhalation, and after recognizing the breathing state of the patient according to the change in the correlation data, the method further comprises:
determining whether the recognized breathing state of the patient matches a current ventilation mode of the ventilation apparatus, and outputting a determination result.

10. The method of claim 1, wherein the breathing state of the patient comprises at least one of assisted inhalation and assisted exhalation, the gas flow rate is a respiratory flow rate, and recognizing the breathing state of the patient according to the change in the correlation data comprises:
determining that the breathing state of the patient is assisted inhalation when the correlation data is greater than zero; and
determining that the breathing state of the patient is assisted exhalation when the correlation data is less than zero.

11. The method of claim 1, wherein the breathing state of the patient comprises at least one of assisted inhalation and assisted exhalation, the gas flow rate is the gas supply flow rate, and recognizing the breathing state of the patient according to the change in the correlation data comprises:
determining that the breathing state of the patient is assisted inhalation when the correlation data rises; and
determining that the breathing state of the patient is assisted exhalation when the correlation data drops.

12. The method of claim 1, wherein the correlation data represents a fluctuation of the patient's breathing and is capable of amplifying small respiratory fluctuations, so as to recognize the breathing state of the patient.

13. The method of claim 1, wherein the correlation equation is:

$$\mathrm{Corr}(k) = \sum_{i=k-n-1}^{k} \mathrm{Flow}\,(i) * \mathrm{Pressure}\,(i)$$

wherein Corr(k) represents the correlation data of the airway pressure and the gas flow rate at a moment k, Flow (i) represents the gas flow rate at a moment i, Pressure (i) represents the airway pressure at the moment i, and n represents a number of a sampled value.

14. The method of claim 1, wherein the correlation data represents a phase correlation between the gas flow rate and the airway pressure.

15. A ventilation apparatus comprising a breathing recognition device, a gas source, a respiration pipeline, a display, and a controller, wherein
the gas source provides a gas during mechanical ventilation;
the respiration pipeline is connected to the gas source and provides an inspiratory path and an expiratory path during the mechanical ventilation;
the breathing recognition device is connected to the respiration pipeline and the controller, and is configured for recognizing a breathing state of a patient during the mechanical ventilation;
the breathing recognition device comprises:
one or more sensors that is configured for acquiring an airway pressure and a gas flow rate during the mechanical ventilation, wherein the gas flow rate is a respiratory flow rate or a gas supply flow rate; and
a processor that is configured for calculating correlation data indicating a correlation between the airway pressure and the gas flow rate according to the airway pressure and the gas flow rate using a correlation equation, and recognizing the breathing state of the patient according to a change in the correlation data;
the controller is further connected to the gas source and controls a process of the mechanical ventilation by controlling the ventilation apparatus to switch a ventilation mode according to the recognized breathing state of the patient; and
the display is connected to the processor and displays a respiratory waveform during the mechanical ventilation;
wherein the breathing state of the patient comprises at least one of spontaneous inhalation and spontaneous exhalation: when the gas flow rate is the gas supply flow rate, the processor is configured for recognizing the breathing state of the patient according to the change in the correlation data, comprises:
determining a parameter baseline corresponding to the correlation data;
determining that the breathing state of the patient is spontaneous exhalation when the correlation data is greater than the parameter baseline and a difference between the correlation data and the parameter baseline is greater than a third preset threshold; and
determining that the breathing state of the patient is spontaneous inhalation when the correlation data is less than the parameter baseline and the difference between the correlation data and the parameter baseline is greater than a fourth preset threshold.

16. The ventilation apparatus of claim 15, wherein when the gas flow rate is the respiratory flow rate, the processor is configured for:
determining that the breathing state of the patient is spontaneous inhalation when the correlation data is greater than a first preset threshold; and
determining that the breathing state of the patient is spontaneous exhalation when the correlation data is less than a second preset threshold.

17. The ventilation apparatus of claim 15, wherein the breathing state of the patient comprises at least one of assisted inhalation and assisted exhalation;
after recognizing the breathing state of the patient according to the change in the correlation data, the processor is configured for determining whether the recognized breathing state of the patient matches a current ventilation mode of the ventilation apparatus, and outputting a determination result.

18. The ventilation apparatus of claim 15, wherein the breathing state of the patient comprises at least one of assisted inhalation and assisted exhalation;
when the gas flow rate is the respiratory flow rate, the processor is configured for:
determining that the breathing state of the patient is assisted inhalation when the correlation data is greater than zero; and
determining that the breathing state of the patient is assisted exhalation when the correlation data is less than zero;
when the gas flow rate is the gas supply flow rate, the processor is configured for:
determining that the breathing state of the patient is assisted inhalation when the correlation data rises; and
determining that the breathing state of the patient is assisted exhalation when the correlation data drops.

19. The ventilation apparatus of claim 15, wherein the breathing state of the patient comprises asphyxia, and the processor is configured for determining that the breathing state of the patient is asphyxia when the correlation data has a fluctuation range less than a preset fluctuation range threshold.

20. The ventilation apparatus of claim 15, wherein the processor determining the parameter baseline corresponding to the correlation data comprises:
calculating the correlation data in a first time period; and
performing low-pass filtering on the correlation data in the first time period to obtain the parameter baseline.

* * * * *